(12) United States Patent
Culberson

(10) Patent No.: US 12,220,652 B2
(45) Date of Patent: Feb. 11, 2025

(54) MICROFLUIDIC PLATFORM FOR REFRIGERATION INDUCED PHASE SEPARATION OF AQUEOUS-ACETONITRILE SOLUTIONS

(71) Applicant: Georgia Tech Research Corporation, Atlanta, GA (US)

(72) Inventor: Austin Lance Culberson, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 487 days.

(21) Appl. No.: 17/597,953

(22) PCT Filed: Jul. 31, 2020

(86) PCT No.: PCT/US2020/044482
§ 371 (c)(1),
(2) Date: Jan. 30, 2022

(87) PCT Pub. No.: WO2021/022151
PCT Pub. Date: Feb. 4, 2021

(65) Prior Publication Data
US 2022/0288508 A1 Sep. 15, 2022

Related U.S. Application Data

(60) Provisional application No. 62/881,715, filed on Aug. 1, 2019.

(51) Int. Cl.
*B01D 17/00* (2006.01)
*B01D 17/12* (2006.01)
(Continued)

(52) U.S. Cl.
CPC .......... *B01D 17/005* (2013.01); *B01D 17/00* (2013.01); *B01D 17/12* (2013.01);
(Continued)

(58) Field of Classification Search
CPC ...... B01D 17/005; B01D 17/00; B01D 17/12; B01L 3/502761; B01L 7/52; B01L 2200/0652; B01L 2300/1894
(Continued)

(56) References Cited

U.S. PATENT DOCUMENTS

| 6,875,619 B2 | 4/2005 | Blackburn |
| 9,028,773 B2 | 5/2015 | Ganesan |

(Continued)

FOREIGN PATENT DOCUMENTS

| WO | 2004108287 A1 | 12/2004 |
| WO | 2005108620 A2 | 11/2005 |
| WO | 2015076865 A1 | 5/2015 |

OTHER PUBLICATIONS

Wang et al., Microfluidic distillation chip for methanol concentration detection, Analytica Chimica Acta, vol. 912, Mar. 17, 2016, pp. 97-104.*

(Continued)

*Primary Examiner* — Fred Prince
(74) *Attorney, Agent, or Firm* — Troutman Pepper Locke LLP; Ryan A. Schneider; Chris N. Davis

(57) ABSTRACT

An embodiment of the disclosed technology provides a microfluidic cooling device including a microfluidic pathway and a thermoelectric cooling element. The microfluidic pathway can include an inlet to receive a sample at a first temperature and an outlet to output a first phase and second phase of the sample at a second temperature. The sample can include a first liquid, a second liquid, and a plurality of soluble particles. The first phase can include the first liquid and a portion of the soluble particles that is more soluble in the first liquid than second liquid. The second phase can include the second liquid and a portion of the soluble particles that more soluble in the second liquid than first liquid. The thermoelectric cooling element can be in thermal (Continued)

communication with the microfluidic pathway and can transition the sample from the first temperature to the second temperature.

33 Claims, 10 Drawing Sheets

(51) Int. Cl.
    *B01L 3/00*         (2006.01)
    *B01L 7/00*         (2006.01)
    *G01N 33/50*      (2006.01)

(52) U.S. Cl.
    CPC .......... *B01L 3/502761* (2013.01); *B01L 7/52* (2013.01); *B01L 2200/0652* (2013.01); *B01L 2300/1894* (2013.01); *G01N 33/50* (2013.01)

(58) Field of Classification Search
    USPC ................................................ 210/775, 774
    See application file for complete search history.

(56) References Cited

U.S. PATENT DOCUMENTS 9,387,478 B2    7/2016    Bergstedt et al.
9,752,185 B2    9/2017    Boronkay et al.

OTHER PUBLICATIONS

Abdelgawad et al., Hybrid microfluidics: A digital-to-channel interface for in-line sample processing and chemical separations, Lab On A Chip, vol. 9, No. 8, Apr. 21, 2009, pp. 1046-1051.*
International Search Report and Written Opinion For International Application No. PCT/US2020/044482 dated Oct. 14, 2020.
Valente Inês Maria; Gonçalves Luís Moreira; Rodrigues José António: "Another glimpse over the salting-out assisted liquid-liquid extraction in acetonitrile/water mixtures", Journal of Chromatography A, vol. 1308, Aug. 8, 2013 (Aug. 8, 2013), pp. 58-62, XP028700756.
Yang et al.: "A comprehensive review of micro-distillation methods", Chemical Engineering Journal, vol. 313, Apr. 1, 2017 (Apr. 1, 2017), pp. 1509-1520, XP029900704.

* cited by examiner

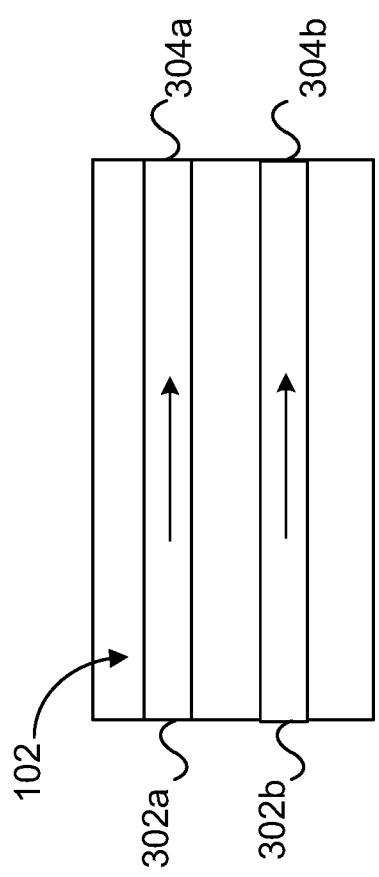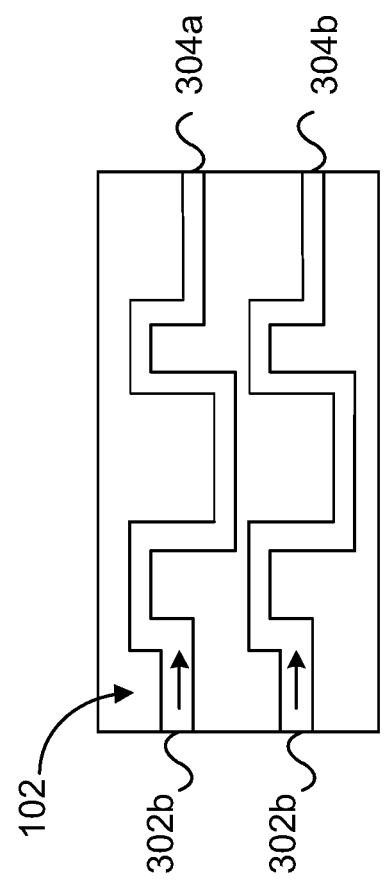

MICROFLUIDIC PLATFORM FOR REFRIGERATION INDUCED PHASE SEPARATION OF AQUEOUS-ACETONITRILE SOLUTIONS

CROSS-REFERENCE TO RELATED APPLICATIONS

This application claims priority, and benefit under 35 U.S.C. § 119(e), to U.S. Provisional Patent Application No. 62/881,715 filed 1 Aug. 2019. The disclosure of the prior application is hereby incorporated by reference as if fully set forth below.

STATEMENT REGARDING GOVERNMENT SUPPORT

This invention was made with government support under Grant No. 1648035 awarded by the National Science Foundation. The government has certain rights in the invention.

FIELD OF DISCLOSURE

The disclosed technology relates generally to phase separation, and more particularly to, systems and methods for temperature induced liquid-liquid phase separation.

BACKGROUND

A variety of analytical techniques rely on preparatory steps to aid in the analysis of complex solutions. Various forms of sample preparation have been developed and implemented including, but not limited to, solid phase extraction, liquid chromatography, filtration, and liquid-liquid extraction; such techniques are still hampered by a variety of factors.

For example, sample preparation workflows can be limited by manual and lengthy steps that are not amenable to rapid, repeatable, inline analysis. Additionally, traditional separation techniques can have processing times from minutes to hours. Solid phase extraction and chromatography can effectively remove many interfering contaminants. However, these methods can be sensitive to clogging, involve high operating costs, require time consuming separations which can limit throughput, experience complications with dilution and carryover, and often require the need for specific knowledge of the sample to guide selection of the stationary and mobile phases. Filtration schemes such as microdialysis can be used for separation of significantly differing analytes based on molecular weight but can be limited in their ability to separate similarly sized analyte classes and are also prone to clogging.

Liquid-liquid extraction can rely on mass transfer between separate, distinct phases for isolation of analytes via physiochemical differences. Liquid-liquid extraction has largely been confined to the use of solvent pairs normally considered immiscible such that distinct phases are present at all times, thus limiting mass transfer and preventing adaptive control. Certain systems of solutions do exist in which phase separation can be initiated via temperature fluctuation, particularly solutions of acetonitrile and water which separate into distinct phases when cooled. When a freezer is used to induce separation of such solutions, only a single cooling temperature can be applied, thereby limiting variable temperature control that can be based on composition, volume, and other characteristics of the solution. This separation technique can also require extensive cooling periods within a freezer, reducing throughput and is not amenable to automated analytical workflows.

SUMMARY

These and other problems can be addressed by the technologies described herein. Examples of the present disclosure relate generally to systems and methods for temperature induced liquid-liquid phase separation.

The disclosed technology can include a microfluidic cooling device for liquid-liquid phase separation. The microfluidic cooling device can include a first microfluidic pathway and a thermoelectric cooling element. The first microfluidic pathway can include one or inlets configured to receive a sample at a first temperature, the sample comprising a first liquid, a second liquid, and a plurality of soluble particles. The first liquid and the second liquid can be substantially miscible at the first temperature. The first microfluidic pathway can include one or more outlets configured to output a first phase of the sample and a second phase of the sample at a second temperature. The first phase can include a majority of the first liquid and a first portion of the plurality of soluble particles, the first portion being more soluble in the first liquid than the second liquid. The second phase can include a majority of the second liquid and a second portion of the plurality of soluble particles, the second portion being more soluble in the second liquid than the first liquid. The thermoelectric cooling element can be in thermal communication with at least a portion of the first microfluidic pathway, and configured to transition the sample from the first temperature to the second temperature.

In any of the embodiments disclosed herein, the first liquid can be water.

In any of the embodiments disclosed herein, the second liquid can be acetonitrile.

In any of the embodiments disclosed herein, the first liquid and the second liquid can be substantially immiscible at the second temperature.

In any of the embodiments disclosed herein, the sample can further include a plurality of analytes. The plurality of analytes can be homogenously distributed throughout the sample at the first temperature.

In any of the embodiments disclosed herein, the plurality of analytes can be more soluble in the first liquid than the second liquid.

In any of the embodiments disclosed herein, the first phase can include the plurality of analytes.

In any of the embodiments disclosed herein, the plurality of analytes can be more soluble in the second liquid than the first liquid.

In any of the embodiments disclosed herein, the second phase can include the plurality of analytes.

In any of the embodiments disclosed herein, the first temperature can be above a phase transition temperature of the sample.

In any of the embodiments disclosed herein, the second temperature can be below a phase transition temperature of the sample.

In any of the embodiments disclosed herein, the thermoelectric cooling element can transition the sample from the first temperature to the second temperature within 60 seconds.

In any of the embodiments disclosed herein, the first microfluidic pathway can include one or more flow channels configured to direct the sample from the one or more inlets to the one or more outlets.

In any of the embodiments disclosed herein, the one or more flow channels can include one or more tubes configured to direct the sample from the one or more inlets to the one or more outlets.

In any of the embodiments disclosed herein, the one or more tubes can have an inner diameter of between approximately 10 microns to approximately 250 microns.

In any of the embodiments disclosed herein, the first microfluidic pathway can include a mixing portion configured to homogenously distribute the plurality of analytes within the sample at the first temperature; and a separation portion in thermal communication with the thermoelectric cooling element and configured to separate the sample into the first phase and the second phase at the second temperature.

In any of the embodiments disclosed herein, the first microfluidic pathway can be interchangeable with a second microfluidic pathway, the first microfluidic pathway having a first set of dimensions and the second microfluidic pathway having a second set of dimensions different than the first set of dimensions.

In any of the embodiments disclosed herein, the first microfluidic pathway can be configured to continuously receive the sample via the one or more inlets; and continuously output the first phase of the sample and the second phase of the sample via the one or more outlets.

In any of the embodiments disclosed herein, the microfluidic pathway can be configured to receive the sample via the one or more inlets; maintain the sample within the microfluidic pathway for a predetermined amount of time; and output the first phase of the sample and the second phase of the sample via the one or more outlets.

In any of the embodiments disclosed herein, the microfluidic cooling device can further include a cover disposed proximate the microfluidic pathway.

In any of the embodiments disclosed herein, the cover can be transparent.

In any of the embodiments disclosed herein, the microfluidic pathway can be microfabricated into the cover, the cover being directly bonded to the thermoelectric cooling element.

In any of the embodiments disclosed herein, the microfluidic cooling device can further include one or more sensors configured to determine a temperature of the thermoelectric cooling element.

In any of the embodiments disclosed herein, an exterior surface of the microfluidic cooling device can include insulating material.

The disclosed technology can further include a microfluidic system for liquid-liquid phase separation including a microfluidic cooling device and a controller. The microfluidic cooling device can include a first microfluidic pathway and a thermoelectric cooling element. The first microfluidic pathway can include one or more inlets configured to receive a sample at a first temperature. The sample can include a first liquid, a second liquid, and a plurality of soluble particles. The first liquid and the second liquid can be substantially miscible at the first temperature. The first microfluidic pathway can include one or more outlets configured to output a first phase of the sample and a second phase of the sample at a second temperature. The first phase can include a majority of the first liquid and a first portion of the plurality of soluble particles, the first portion being more soluble in the first liquid than the second liquid. The second phase can include a majority of the second liquid and a second portion of the plurality of the soluble particles, the second portion being more soluble in the second liquid than the first liquid.

The thermoelectric cooling element can be in thermal communication with at least a portion of the microfluidic pathway and configured to transition the sample from the first temperature to the second temperature. The controller can be in operative communication with the microfluidic cooling device and configured to cause the thermoelectric cooling element to transition the sample from the first temperature to the second temperature.

In any of the embodiments disclosed herein, the first liquid can be water and the second liquid can be acetonitrile.

In any of the embodiments disclosed herein, the first liquid and the second liquid can be substantially immiscible at the second temperature.

In any of the embodiments disclosed herein, the sample can further include a plurality of analytes, the plurality of analytes being homogenously distributed throughout the sample at the first temperature.

In any of the embodiments disclosed herein, the plurality of analytes can be more soluble in the first liquid than the second liquid.

In any of the embodiments disclosed herein, the first phase can include the plurality of analytes.

In any of the embodiments disclosed herein, the plurality of analytes can be more soluble in the second liquid than the first liquid.

In any of the embodiments disclosed herein, the second phase can include the plurality of analytes.

In any of the embodiments disclosed herein, the controller can include a graphical user interface configured to receive user inputs for a plurality of operative parameters.

In any of the embodiments disclosed herein, the microfluidic cooling system can further include a plurality of sensors configured to measure a temperature of the thermoelectric cooling element.

In any of the embodiments disclosed herein, the microfluidic cooling system can further include a power supply in operative communication with the thermoelectric cooling element.

In any of the embodiments disclosed herein, the controller can be further configured to regulate a temperature of the thermoelectric cooling element.

In any of the embodiments disclosed herein, the temperature of the thermoelectric cooling element can be regulated based at least in part on phase equilibrium data of the sample.

In any of the embodiments disclosed herein, the microfluidic cooling system can further include a plurality of valves configured to insert a first predetermined amount of the first liquid and a second predetermined amount of the second liquid via the one or more inlets and output a first predetermined amount of the first phase and a second predetermined amount of the second phase.

In any of the embodiments disclosed herein, the plurality of valves can be in electronic communication with the controller, the plurality of valves configured to automatically insert the second liquid into the microfluidic cooling device upon the first liquid being inserted into the microfluidic cooling device.

The disclosed technology can also include a method of liquid-liquid phase separation including inserting a sample into a microfluidic cooling device at a first temperature via one or more inlets, the sample including a first liquid, a second liquid, and a plurality of soluble particles, the first liquid and the second liquid being substantially miscible at the first temperature. The method can further include cooling the sample to a second temperature. The method can further include separating, as a result of the cooling, the sample into a first phase and a second phase. The first phase can include a majority of the first liquid and a first portion of the plurality of soluble particles, the first portion being more soluble in the first liquid than the second liquid. The second phase can include a majority of the second liquid and a second portion of the plurality of soluble particles, the second portion being more soluble in the second liquid than the first liquid.

In any of the embodiments disclosed herein, the first liquid can be water and the second liquid can be acetonitrile.

In any of the embodiments disclosed herein, the sample can further include a plurality of analytes homogenously distributed throughout the sample at the first temperature.

In any of the embodiments disclosed herein, inserting the sample into the microfluidic cooling device can include inserting the first liquid before inserting the second liquid.

In any of the embodiments disclosed herein, inserting the sample into the microfluidic cooling device can include inserting the first liquid and the second liquid simultaneously.

In any of the embodiments disclosed herein, the second temperature can be below a phase transition temperature of the sample.

In any of the embodiments disclosed herein, separating the sample into the first phase and the second phase can occur approximately 60 seconds.

In any of the embodiments disclosed herein, separating the sample into the first phase and the second phase can occur within approximately 60 seconds and approximately 5 minutes.

In any of the embodiments disclosed herein, the method can further include maintaining the sample within the microfluidic cooling device for a predetermined time at the second temperature while separating the sample into the first phase and the second phase; and outputting the first phase and the second phase from the microfluidic cooling device via one or more outlets.

In any of the embodiments disclosed herein, the sample can be continuously inserted into the microfluidic cooling device.

In any of the embodiments disclosed herein, the method can further include removing the first phase from the microfluidic device via a first outlet and removing the second phase from the microfluidic device via a second outlet.

In any of the embodiments disclosed herein, the method can further include analyzing the first phase.

In any of the embodiments disclosed herein, the method can further include analyzing the second phase.

These and other aspects of the present invention are described in the Detailed Description below and the accompanying figures. Other aspects and features of embodiments of the present invention will become apparent to those of ordinary skill in the art upon reviewing the following description of specific, exemplary embodiments of the present invention in concert with the figures. While features of the present invention may be discussed relative to certain embodiments and figures, all embodiments of the present invention can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present invention

BRIEF DESCRIPTION OF THE FIGURES

Reference will now be made to the accompanying figures, which are not necessarily drawn to scale, and wherein:

FIGS. 3A-3F are schematic diagrams of example microfluidic pathways of a microfluidic cooling device, according to some aspects of the present disclosure.

DETAILED DESCRIPTION

Figure 1:
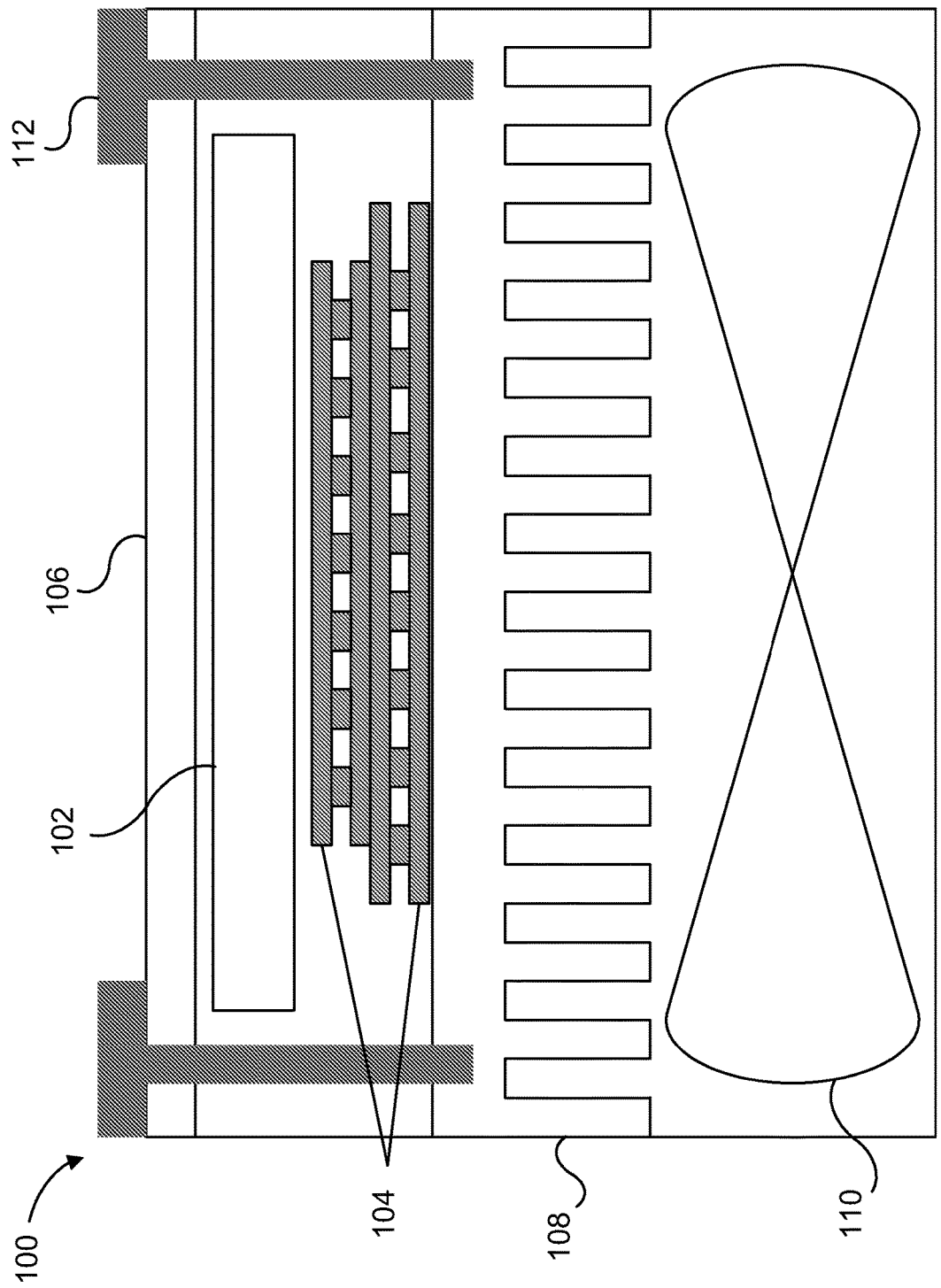
FIG. 1 is an illustration of a front view of a microfluidic cooling device, according to some aspects of the present disclosure.

The disclosed technology relates to a microfluidic cooling device for liquid-liquid phase separation. A sample including a first liquid, a second liquid, and a plurality of soluble particles, can be inserted into a microfluidic cooling device. The sample can be inserted into the microfluidic cooling device at a first temperature such that the first liquid and second liquid are substantially miscible and the soluble particles are homogenously distributed throughout. At least a portion of the microfluidic pathway can be in thermal communication with a thermoelectric cooling element of the microfluidic cooling device. Upon initiation of thermoelectric cooling, the thermoelectric cooling element can transition the sample from the first temperature to a second temperature. At the second temperature, the sample can separate into a first phase including a majority of the first liquid and a portion of the soluble particles that is more soluble in the first liquid than the second liquid, and a second phase including a majority of the second liquid and a portion of the soluble particles that is more soluble in the second liquid than the first liquid.

The disclosed technology will be described more fully hereinafter with reference to the accompanying drawings. This disclosed technology can, however, be embodied in many different forms and should not be construed as limited to the examples set forth herein. The components described hereinafter as making up various elements of the disclosed technology are intended to be illustrative and not restrictive. Many suitable components that would perform the same or similar functions as components described herein are intended to be embraced within the scope of the disclosed electronic devices and methods. Such other components not described herein may include, but are not limited to, for example, components developed after development of the disclosed technology.

In the following description, numerous specific details are set forth. But it is to be understood that examples of the disclosed technology can be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

Unless otherwise specified, the use of the ordinal adjectives "first," "second," "third," etc., to describe a common object, merely indicate that different instances of like objects are being referred to, and are not intended to imply that the objects so described should be in a given sequence, either temporally, spatially, in ranking, or in any other manner.

Unless otherwise specified, the use of the term "hydrophilic" refers to any particle, plurality of particles, analyte, plurality of analytes, or any chemical constituent that is entirely hydrophilic, substantially hydrophilic, or has a polarity tendency that is more hydrophilic than hydrophobic.

Unless otherwise specified, the use of the term "hydrophobic" refers to any particle, plurality of particles, analyte, plurality of analytes, or any chemical constituent that is entirely hydrophobic, substantially hydrophobic, or has a polarity tendency that is more hydrophobic than hydrophilic.

FIG. 1 illustrates a front view of an example microfluidic cooling device 100. The microfluidic cooling device 100 can include a thermoelectric cooling element 104 disposed proximate a heat sink 108. The thermoelectric cooling element 104 can be many different cooling elements (or coolers) known in the art, including, but not limited to, a Peltier cooler. The microfluidic cooling device 100 can include any number of thermoelectric cooling elements 104. As illustrated in FIG. 1, the microfluidic cooling device 100 can include two thermoelectric cooling elements 104. Thermoelectric cooling can be initiated when electrical power is supplied the thermoelectric cooling element 104 via any standard power supply. During thermoelectric cooling via the thermoelectric cooling element 104, one face of the thermoelectric cooling element 104 can become cooled, while an opposite face can become heated. The heated face of the thermoelectric cooling element 104 can be positioned proximate the heat sink 108 such that the heat sink 108 can absorb heat being transferred from the cooled face to the heated face. A fan 102 can be positioned proximate the heat sink 104 to facilitate thermoelectric cooling.

The microfluidic cooling device 100 can further include a microfluidic pathway 102 configured to receive a sample 200. As the sample 200 flows through the microfluidic pathway 102, the sample 200 can undergo thermoelectric cooling. During thermoelectric cooling, the sample 200 can transition from an input temperature to a separation temperature. A microfluidic pathway 102 can be positioned proximate the thermoelectric cooling element 104. The microfluidic pathway 102 can be positioned proximate the cooled face of the thermoelectric cooling element 104 such that the sample 200 flowing through the microfluidic pathway 102 can be cooled. In some embodiments, only a portion of the microfluidic pathway 102 can be in thermal communication with the thermoelectric cooling element 104. Alternatively, in some embodiments, an entire length of the microfluidic pathway 102 can be in thermal communication with the thermoelectric cooling element 104. In some embodiments, the microfluidic pathway 102 is positioned directly on the thermoelectric cooling element 104. By way of example, the microfluidic pathway 102 can be positioned directly on the thermoelectric cooling element 104 using any attachment means, including an adhesive, or without an attachment means.

In some embodiments, a cover 106 can be placed proximate the microfluidic pathway 102. The cover 106 can secure the microfluidic pathway 102 to the thermoelectric cooling element 104. The cover 106 can be affixed to the microfluidic cooling device 100 via any attachment means, including but not limited to, a screw, bolt, adhesives, welding, or the like. In some embodiments, the cover 106 can be transparent to provide a visual indicator of the microfluidic pathway 102 and/or the sample 200 within the microfluidic pathway 102 during operation of the microfluidic cooling device 100.

The microfluidic cooling device 100 can have an exterior housing made of insulating material. The exterior housing can optimize thermoelectric cooling of the sample 200. In some embodiments, the microfluidic cooling device 100 can be portable, thereby facilitating use and transport to various locations.

Figure 2:
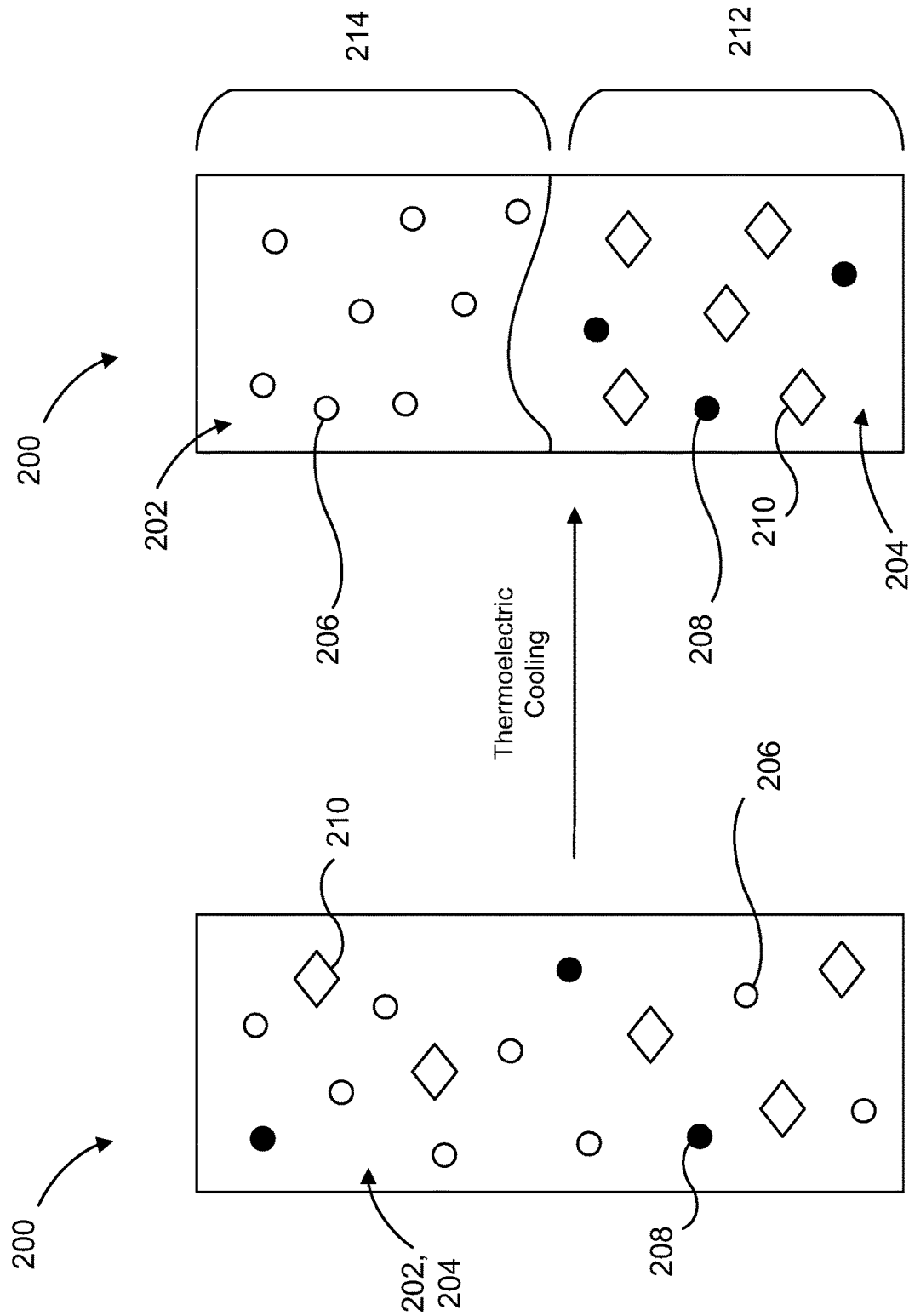
FIG. 2 is a schematic diagram of a sample prior to thermoelectric cooling and the sample after thermoelectric cooling, according to some aspects of the present disclosure.

FIG. 2 illustrates a schematic diagram of the sample 200 prior to thermoelectric cooling and after thermoelectric cooling. The sample 200 inserted into the microfluidic pathway 102 can include a first liquid 202 and a second liquid 204. The first liquid 202 can be water, including deionized water. The second liquid 204 can be acetonitrile. The sample 200 can include a plurality of soluble particles, including hydrophobic particles 206 and hydrophilic particles 208. The hydrophobic particles 206 and the hydrophilic particles 208 can be substantially dissolved within the sample 200 when the sample is inserted into the microfluidic pathway 102 at the input temperature.

The sample 200 can be inserted into the microfluidic cooling device 100 at the input temperature. The input temperature can be above a phase transition temperature of the sample 200. In some embodiments, the input temperature can be based at least in part on the composition of the sample 200. In some embodiments, the input temperature can be between approximately 20° C. and approximately 30° C. At the input temperature, the first liquid 202 and the second liquid 204 can be substantially miscible, and the hydrophobic particles 206 and the hydrophilic particles 208 can be homogenously distributed throughout the sample 200.

In some embodiments, the sample 200 can include a plurality of analytes 210. The plurality of analytes 210 can be metabolites, chemical constituents, or any component of interest in an analytical procedure. The plurality of analytes 210 can be of any molecular weight or chemical composition. By way of example, the plurality of analytes 210 can be amino acids, peptides, lipids, metabolites, proteins, or the like. The plurality of analytes 210 can be entirely or substantially hydrophilic. In some embodiments, the plurality of analytes 210 can be more hydrophilic than hydrophobic. Alternatively, in some embodiments, the plurality of analytes 210 can be entirely or substantially hydrophobic. In some embodiments, the plurality of analytes 210 can be more hydrophobic than hydrophilic. In some embodiments, the plurality of analytes 210 can include hydrophilic analytes and hydrophobic analytes. The plurality of analytes 210 can be dissolved within the sample 200 and homogenously distributed throughout the sample 200 when the sample 200 is inserted into the microfluidic cooling device 100 at the input temperature.

When the microfluidic cooling device 100 is operating, as the sample 200 flows through the microfluidic pathway 102, the sample 200 can undergo thermoelectric cooling via the thermoelectric cooling element 104 and thereby transition from the input temperature to the separation temperature. Upon the thermoelectric cooling, the first liquid 202 and the second liquid 204 can become substantially immiscible, thereby separating from one another into a first phase 212 and a second phase 214. The temperature at which the sample 200 can separate into the first phase 211 and the second phase 214 can be below the phase transition temperature of the sample 200. The separation temperature can depend on the composition of the sample 200. By way of example, when the sample 200 includes water as the first liquid 202 and acetonitrile as the second liquid 204, and no additional solutes or analytes, separation into the first phase 212 and the second phase 214 can occur at a separation temperature of approximately −1.3° C. Alternatively, the sample 200 can separate into the first phase 212 and the second phase 214 at a separation temperature of less than −1.3° C. In some embodiments, the sample 200 can separate into the first phase 212 and the second phase 212 at a temperature of between approximately −10° C. and approximately −20° C. In some embodiments, the thermoelectric cooling element 104 can transition the sample 200 from the input temperature to the separation temperature within 60 seconds. In some embodiments, the thermoelectric cooling element 104 can transition the sample 200 from the input temperature to the separation temperature within between approximately 61 seconds and approximately 5 minutes. In some embodiments, the thermoelectric cooling element 104 can transition the sample 200 from the input temperature to the separation temperature within between approximately 5 minutes and approximately 30 minutes. The ability to transition the sample from the input temperature to the separation temperature rapidly, and thereby separating the sample 200 into the first phase 212 and the second phase 214 rapidly can provide increased throughput of sample analysis as compared to other liquid-liquid phase separation methods. Additionally, the rapid nature of the thermoelectric cooling via the thermoelectric cooling device 100 can allow for dynamic, sensitive, and/or reactive analytes 210 to be analyzed.

When the first liquid 202 is water and the second liquid 204 is acetonitrile, the first phase 212 can include a majority of the first liquid 202 and a majority of the hydrophilic particles 208. In some embodiments, the first phase 212 can include all of the hydrophilic particles 208. The second phase 214 can include a majority of the second liquid 204 and a majority of the hydrophobic particles 206. In some embodiments, the second phase 214 can include all of the hydrophobic particles 206. The ratio of the first liquid 202 to second liquid 204 in the first phase 212 and the second phase 214 can depend at least in part on the initial compositions and volumes of the first liquid 202 and the second liquid 204. The ratio of the first liquid 202 and the second liquid 204 in the first phase 212 and the second phase 214 can also depend on the separation temperature. In some embodiments, when the sample 200 separates into the first phase 212 and the second phase 214, the first phase 212 can include approximately all of the first liquid 202 and the second phase 214 can include approximately all of the second liquid 204. Alternatively, and by way of a non-limiting example, the first phase can include approximately 75% of the first liquid 202 and 25% of the second liquid 204, while the second phase can include approximately 75% of the second liquid 204 and approximately 25% of the first liquid 202.

The plurality of analytes 210 can separate into either the first phase 212 or the second phase 214 depending on the polarity of the plurality of analytes 210. By way of example, when the plurality of analytes 210 is more soluble in the first liquid 202 than the second liquid 204, and thereby more hydrophilic or more hydrophilic than hydrophobic, the first phase 212 can include the plurality of analytes 210, as illustrated in FIG. 2. Alternatively, when the plurality of analytes 210 is more soluble in the second liquid 204 than the first liquid 202, and thereby more hydrophobic than hydrophilic, the second phase 214 can include the plurality of analytes 210. When the plurality of analytes 210 includes both hydrophilic analytes and hydrophobic analytes, the first phase 212 can include the portion of the plurality of analytes 210 that is more soluble in the first liquid 202 than the second liquid 204, and thereby more hydrophilic than hydrophobic. The second phase 214 can include the portion of the plurality of analytes 210 that is more soluble in the second liquid 204 than the first liquid 202, and thereby more hydrophobic than hydrophilic. Upon separation, the first phase 212 and the second phase 214 can be outputted from the microfluidic pathway 102 of the microfluidic cooling device 100. The first phase 212 and the second phase 214 can be outputted from the microfluidic cooling device 100 at the separation temperature to ensure the first phase 212 and the second phase 214 remain separated.

FIGS. 3A-3F illustrate schematic diagrams of a top view of the microfluidic pathway 102. The microfluidic pathway 102 can have one or more inlets 302 configured to receive the sample 200, and one or more outlets 304 configured to output the first phase 212 and the second phase 214 upon phase separation. The sample 200 can be inserted into the inlet 302 of the microfluidic pathway 102 using any standard fluidic introduction method or device, including a syringe, a pipette, or the like. Upon separation, the first phase 212 and the second phase 214 can be outputted from the outlet 304 via any standard fluidic output method or device, including suction, a pipette, a syringe, or the like.

The microfluidic pathway 102 can include one or more flow channels configured to direct the sample 200 through the microfluidic cooling device 100 from the inlet 302 to the outlet 304. In some embodiments, the flow channel or flow channels can be a tube or tubes extending from the inlet 302 to the outlet 304. The tube can have an inner diameter of between approximately 10 microns and approximately 250 microns. In some embodiments, adhesives can be used to secure the tube to the thermoelectric cooling element 104 such that the tube and the thermoelectric cooling element 104 are in thermal communication. Alternatively, the cover 106 can be disposed proximate the tube such that the tube and the thermoelectric cooling element 104 can remain in thermal communication. In some embodiments, the microfluidic pathway 102 can include a self-contained microfabricated separation chamber, and the flow channels can be fabricated into the separation chamber using photolithography and standard etching procedures. By way of example, the flow channels can be etched from a silicon substrate or glass substrate. Similarly, in some embodiments, the flow channels can be fabricated from a patterned polydimethylsiloxane (PDMS) substrate bonded to glass. Fully integrated fluidics can provide seamless flow of the sample 200 between the microfluidic pathway 102 and the separation chamber. In some embodiments, the flow channels can be elongated recesses. The recesses can be cut from any material, including a polymeric material, a thermoplastic material, or the like. By way of example, the flow channels can be cut from a 1/16-inch rubber gasket material. The material including the etched flow channels can be affixed directly to the thermoelectric cooling element 104 such that the microfluidic pathway 102 can be in thermal communication with the thermoelectric cooling element 104. The cover 106 can then be positioned to secure the material to the thermoelectric cooling element 104. In some embodiments, the flow channels can be microfabricated into the cover 106. The cover 106 including the flow channels can be affixed directly to the thermoelectric cooling element 104 such that the microfluidic pathway 102 is in thermal communication with the thermoelectric cooling element 104.

Figure 3B:
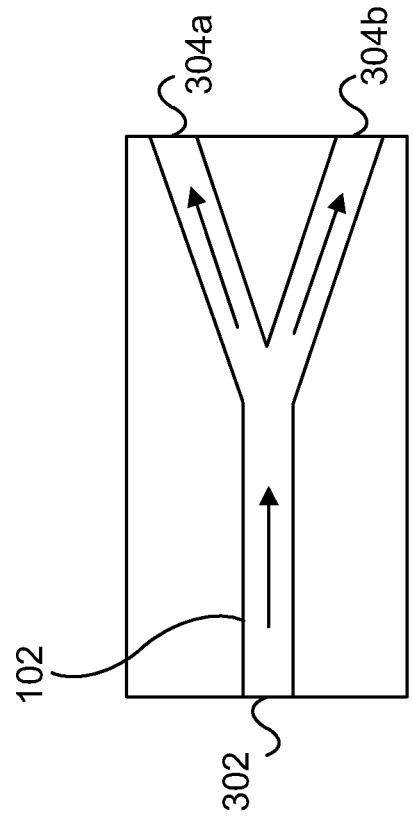
Figure 3D:
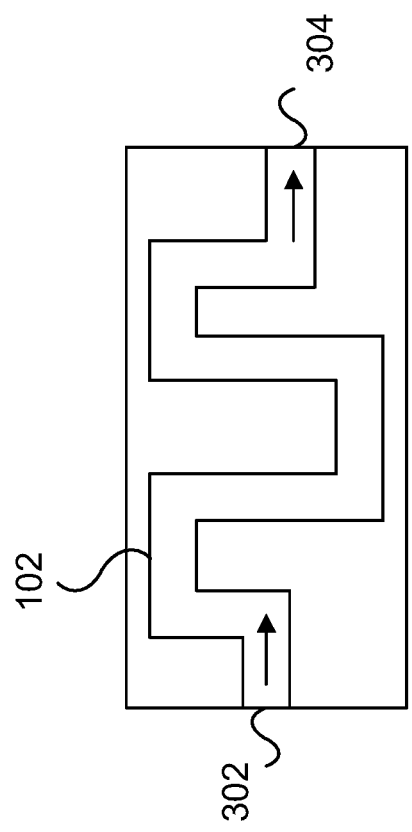
Figure 3A:
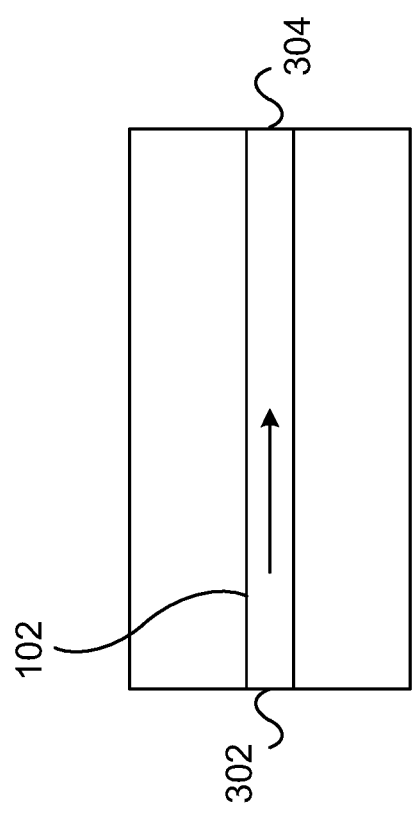
Figure 3C:
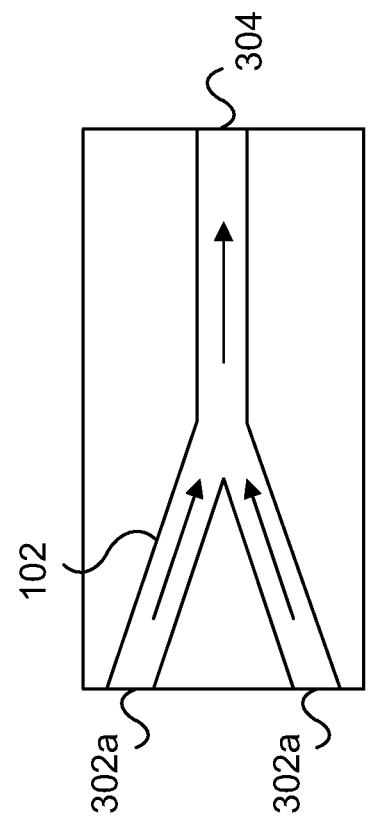

The microfluidic pathway 102 can have a variety of configurations. As illustrated in FIG. 3A, the microfluidic pathway 102 can include a single flow channel (e.g., a single tube or single elongated recess) configured to direct the sample from the inlet 302 to the outlet 304. The single flow channel can be substantially linear. As illustrated in FIG. 3B, the microfluidic pathway 102 can include a single flow channel that can diverge into two distinct flow channels. In this configuration, the sample 200 can be inserted into the microfluidic pathway 102 via the inlet 302 and can be outputted from the microfluidic pathway 102 via a first outlet 304a and a second outlet 304b. In some embodiments, the first phase 212 can exit the microfluidic pathway 102 via the first outlet 304a and the second phase 214 can exit the microfluidic pathway 102 via the second outlet 304b. As illustrated in FIG. 3C, the microfluidic pathway 102 can include two flow channels that can converge into a single flow channel. In this configuration, the microfluidic pathway 102 can include a first inlet 302a and a second inlet 302b and a single outlet 304. As illustrated in FIG. 3D, the microfluidic pathway 102 can have a winding, twisting, and/or serpentine configuration. The microfluidic pathway 102 can include any number of flow channels. As illustrated in FIG. 3E, the microfluidic pathway 102 can include two separate and distinct linear flow channels with each flow channel including an inlet 302a, 302b and an outlet 304a, 304b. As illustrated in FIG. 3F, the microfluidic pathway 102 can include two separate and distinct winding, twisting, and/or serpentine flow channels with each flow channel including an inlet 302a, 302b and an outlet 304a, 304b. When the microfluidic pathway 102 includes multiple flow channels, the sample 200 can be inserted via the inlet 302 into each flow channel, thereby providing a high throughput of separation of the sample 200 into the first phase 212 and the second phase 214. In some embodiments, the configuration and/or dimensions of the microfluidic pathway 102 can be based at least in part on optimizing thermoelectric cooling and phase separation of the sample 200.

Although FIGS. 3A through 3F illustrate various example microfluidic pathways 102, it is contemplated the microfluidic pathway 102 can include any number of flow channels having any dimensions, any number of inlets 302 and outlets 304, and any flow channel configuration.

In some embodiments, the inlet 302 and/or outlet 304 of the microfluidic flow path 102 can be configured to be integrated with an existing fluidic flow path. By way of example, the outlet 304 can be configured to direct the first phase 212 and/or the second phase 214 to mass spectrometry for further analysis. By integrating the microfluidic flow path 102 with an existing fluidic flow path, unintentional loss and/or dilution of the sample 200 can be minimized and analyte concentration for maximum detectability in downstream analysis can be preserved.

In some embodiments, the microfluidic cooling device 100 can be configured to receive any number of microfluidic pathways 102. By way of example, a first microfluidic pathway 102 having a first configuration and a first set of dimensions can be positioned proximate the thermoelectric cooling element 104. Upon thermoelectric cooling and phase separation of the sample 200, the sample 200 can be outputted from the first microfluidic pathway 102. The first microfluidic pathway 102 can then be removed from the microfluidic cooling device 100. Subsequently, a second microfluidic pathway having a second configuration and a second set of dimensions can be positioned proximate the thermoelectric cooling element 104 such that the sample 200 can undergo thermoelectric cooling within the second microfluidic pathway. Accordingly, the first microfluidic pathway 102 can be easily interchanged with a second microfluidic pathway having a different configuration and/or different dimensions such that thermoelectric cooling can be tailored depending on the sample 200 composition, desired composition and volume of the first phase 212 and the second phase 214, and/or separation temperature.

Figure 4:
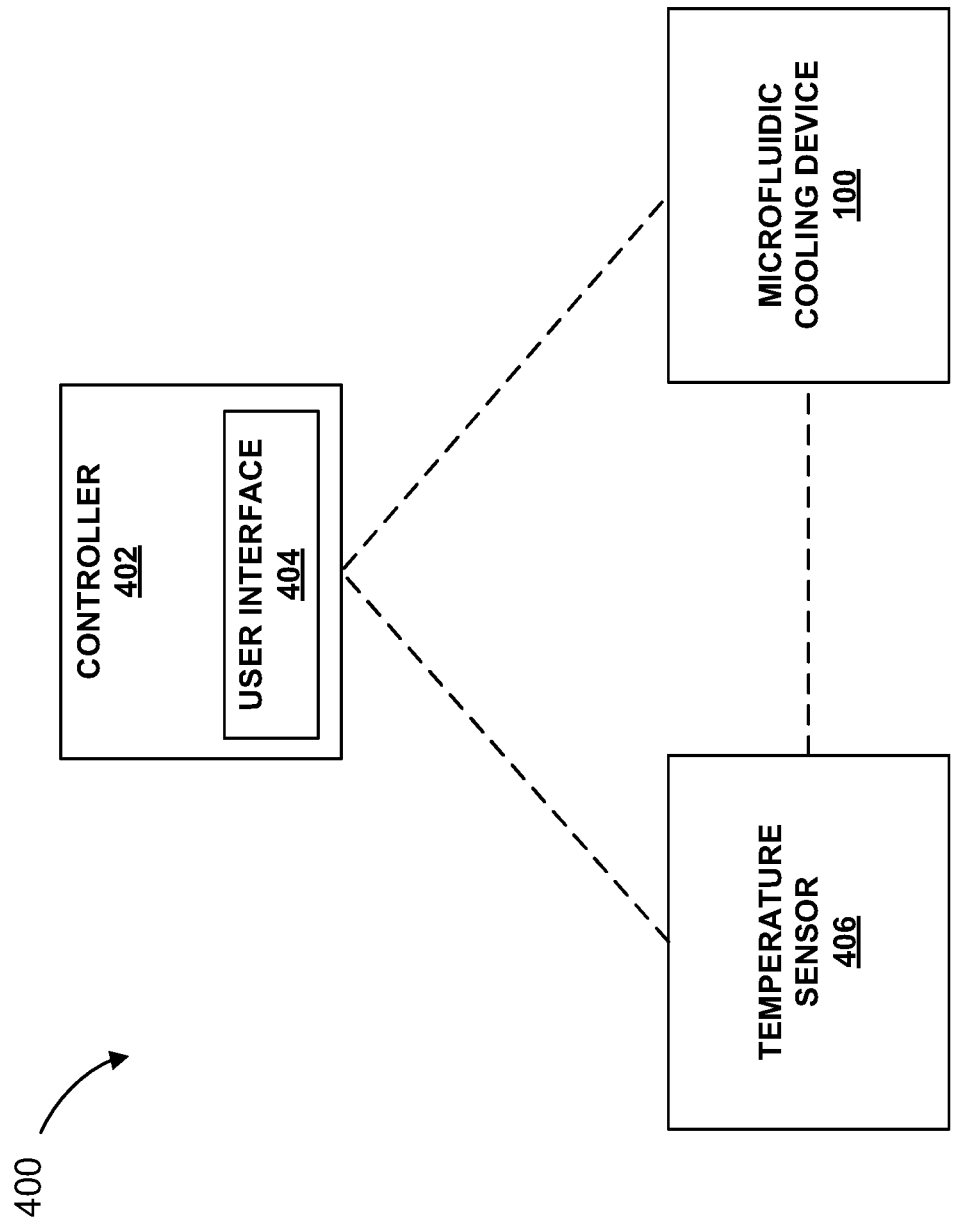
FIG. 4 is a diagram of a microfluidic cooling system, according to some aspects of the present disclosure.

FIG. 4 is a diagram of a microfluidic cooling system 400. The microfluidic cooling system 400 can include the microfluidic cooling device 100, a controller 402, and one or more temperature sensors 406. The controller 402 can be in electrical communication with the microfluidic cooling device 100 and the one or more temperature sensors 406. The controller 402 can be configured to send one or more signals to various components of the microfluidic cooling device 100 and receive one or more signals from various components of the microfluidic cooling device 100 in order to optimize thermoelectric cooling of the sample 200.

The controller 402 can include a graphical user interface 404 for receiving user input for operative parameters of the thermoelectric cooling, thereby allowing a user to tailor the thermoelectric cooling via the microfluidic cooling device 100 based on known characteristics of the sample 200 prior to thermoelectric cooling and desired parameters of the first phase 212 and the second phase 214 upon separation. A user can input data pertaining to characteristics of the sample 200 in order to achieve optimal thermoelectric cooling and the resulting phase separation into the first phase 212 and the second phase 214. By way of example, the user can input data indicative of the sample 200, including but not limited to, chemical composition of the sample 200, volume of the sample 200, ratio of the first liquid 202 to the second liquid 204, characteristics of the hydrophilic particles 206 and hydrophobic particles 208, and characteristics of the plurality of analytes 210. The user can input data indicative of a desired flow rate of the sample 200 through the microfluidic pathway 102. The user can input data indicative of desired characteristics of the first phase 212 and the second phase 214 including compositions of the first phase 212 and/or the second phase 214 and volume fractions of the first phase 212 and/or the second phase 214. Based at least in part on the data inputted and phase equilibrium models, the controller 402 can determine operative parameters of the thermoelectric cooling. By way of example, the controller 402 can determine the separation temperature required to achieve separation of the sample 200 into the first phase 212 and the second phase 214. In this sense, unlike a traditional freezer cooling method to induce phase separation that can only provide a single cooling temperature, the microfluidic cooling device 100 can be configured to provide thermoelectric cooling at a first cooling temperature (e.g., output temperature) for a first sample and upon separation and removal of the first sample, can provide a second cooling temperature for a second sample. The controller 402 can determine an approximate length of time the sample 200 will need to be in thermal communication with the thermoelectric cooling element 104 in order to have phase separation into the first phase 212 and the second phase 214. The controller 402 can further determine volume of a buffer solution, including acetonitrile buffer and/or aqueous buffer, that can be inserted into the microfluidic pathway 102 in order for the desired resulting compositions and volumes to be achieved. After determining operative parameters of thermoelectric cooling of the sample 200, the controller 402 can output one or more signals to various components of the microfluidic cooling device 100 to implement such operative parameters. Unlike traditional liquid-liquid phase separation techniques that were often limited to a single cooling temperature and were unable to specifically tailor phase separation based on characteristics of the sample 200 or desired resulting phases 212,214, the microfluidic cooling system 400 can provide rapid thermoelectric cooling that can be precisely controlled using phase equilibrium data and characteristics of the sample 200.

The microfluidic cooling device 100 can include one or more temperature sensors 406 in electrical communication with the controller 402. A temperature sensor 406 can be disposed on, near, or proximate the thermoelectric cooling element 104 to determine a temperature of the thermoelectric cooling element. A temperature sensor 406 can be disposed proximate the inlet 302 of the microfluidic pathway 102 to determine a temperature of the sample 200 prior to thermoelectric cooling and/or phase separation. A temperature sensor 406 can be disposed proximate the outlet 304 of the microfluidic pathway 102 to determine a temperature of the sample 200 after thermoelectric cooling and/or phase separation. The temperature sensors 406 can provide real-time thermal management and monitoring of the sample 200 during thermoelectric cooling. In some embodiments, the output temperature (e.g., cooling temperature) can be dynamically controlled during thermoelectric cooling by continuous electrical communication between the temperature sensor 406 and the controller 402, such that a user can set the output temperature before thermoelectric cooling and/or vary the output temperature during thermoelectric cooling.

Figure 5A:
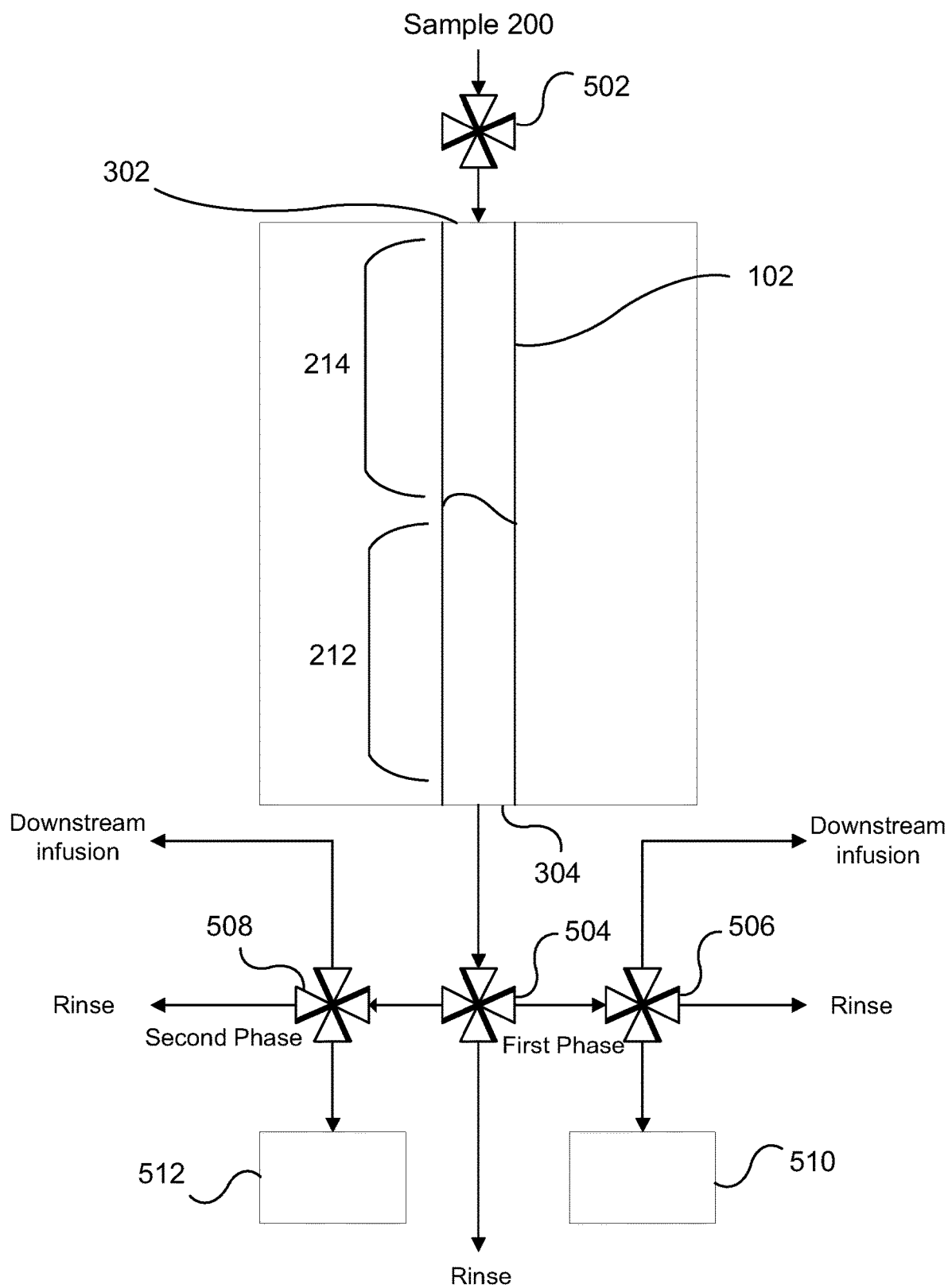
FIG. 5A is a schematic diagram of a microfluidic cooling device configured to operate in a batch mode, according to some aspects of the present disclosure.

FIG. 5A is a schematic diagram of the microfluidic cooling device 100 configured to operate in a batch mode. In the batch mode operation, the sample 200 can be inserted into the microfluidic pathway 102 of the microfluidic cooling device 100. The sample 200 can be maintained within the microfluidic pathway 102 for a predetermined amount of time during which thermoelectric cooling via the thermoelectric cooling element 104 can be initiated and the sample 200 can accordingly separate into the first phase 212 and the second phase 214. The resulting first phase 212 and the second phase 214 can be outputted from the microfluidic pathway 102.

When the microfluidic cooling device 100 is operating in a batch mode, the microfluidic pathway 102 can first be filled with a buffer solution, including an aqueous buffer and/or an acetonitrile buffer, via a first valve 502 prior to inserting the sample 200 into the microfluidic pathway 102. The sample 200 can then be inserted into the microfluidic pathway 102 via the first valve 502. The first valve 502 can be configured to insert a predetermined amount of the sample 200 into the microfluidic pathway 102 at a predetermined rate. In some embodiments, a predetermined amount of the first liquid 202 can be inserted into the microfluidic pathway 102 prior to a predetermined amount of the second liquid 204. Alternatively, a predetermined amount of the second liquid 204 can be inserted into the microfluidic pathway 102 prior to a predetermined amount of the first liquid 202. In some instances, the first liquid 202 and the second liquid 204 can be inserted into the microfluidic pathway simultaneously. As the sample 200 is inserted into the microfluidic pathway 102, the buffer solution can be displaced and can exit the microfluidic pathway 102 via a second valve 504. In some embodiments, the buffer solution that exits the microfluidic pathway 102 can be rinsed and re-inserted into the microfluidic pathway 102 until the desired composition and volume of the sample 200 within the microfluidic pathway 102 is achieved. The first valve 502 and the second valve 504 can then be closed, thereby isolating the sample 200 within the microfluidic pathway 102. The sample 200 can remain within the microfluidic pathway 102 for a predetermined amount of time while thermoelectric cooling via the thermoelectric cooling element 104 is initiated. The thermoelectric cooling via the thermoelectric cooling element 104 can transition the sample 200 from the input temperature to the separation temperature. The temperature sensors 406 can monitor the temperature of the thermoelectric cooling element, and thereby the approximate temperature of the sample 200, to provide feedback to the controller 402. At the separation temperature, the sample 200 can separate into the first phase 212 and the second phase 214. In some embodiments, the first phase 212, including the first liquid (e.g., water) 202 and the plurality of hydrophilic particles 208, can settle to the bottom of the microfluidic pathway, while the second phase 214, including the second liquid (e.g., acetonitrile) 204 and the plurality of hydrophobic particles 208, can be a distinct layer above the first phase 212. Upon separation, the second valve 504 can be configured to remove the first phase 212 and the second phase 214 from the microfluidic pathway 102. In some embodiments, the first phase 212 and the second phase 214 can be removed by applying suction at the outlet 304 of the microfluidic pathway 102.

In some embodiments, after removal, the first phase 212 can be directed to a first fluid reservoir 510 via a third valve 506, and/or the second phase 214 can be directed to a second fluid reservoir 512 via a fourth valve 508. In some embodiments, the first phase 212 within the first fluid reservoir 510 and the second phase 214 within the second fluid reservoir 512 can be subjected to secondary thermoelectric cooling in order to freeze the first phase 212 and the second phase 214 before transport. In some embodiments, after removal, the first phase 212 and/or the second phase 214 can be directly infused into a downstream process flows via the third valve 506 and the fourth valve 508, respectively. After the first phase 212 and the second phase 214 are removed from the microfluidic pathway 102, the microfluidic pathway 102 can be rinsed with a buffer solution in order to prepare the microfluidic pathway 102 for receiving an additional sample or an additional volumetric amount of the same sample 200. The buffer solution can be inserted into the microfluidic pathway 102 via the first valve 502, and the second valve 504, the third valve 506, and the fourth valve 508 can be configured to receive the buffer solution such that the entire system can be rinsed.

Figure 5B:
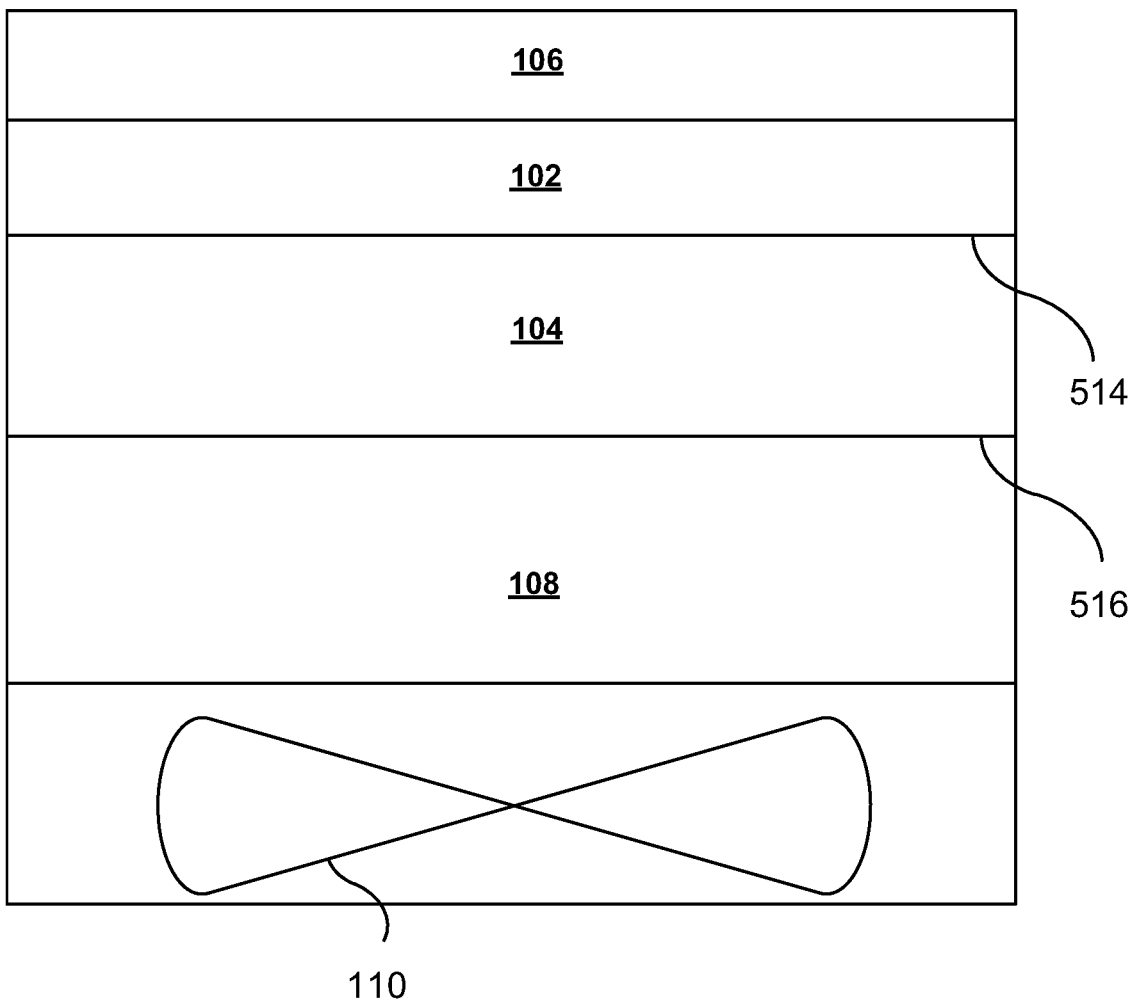
FIG. 5B is a cross-section view of the microfluidic cooling device of FIG. 5A, according to some aspects of the present disclosure.

FIG. 5B is a cross-section view of the microfluidic cooling device 100 of FIG. 5A. The microfluidic pathway 102 can be disposed proximate the thermoelectric cooling element 104. In some embodiments, the microfluidic pathway 102 can be disposed directly on the thermoelectric cooling element 104. The cover 106 can be positioned to secure the microfluidic pathway 102 to the thermoelectric cooling element 104 such that the microfluidic pathway 102 can be in thermal communication with the thermoelectric cooling element 104. Although in FIG. 5B, the microfluidic pathway 102 is in thermal communication with the thermoelectric cooling element 104 over the entire length of the microfluidic pathway 102, it is contemplated that in some embodiments only a portion of the microfluidic pathway 102 can be in thermal communication with the thermoelectric cooling element 104. When the thermoelectric cooling is initiated by the controller 402 and a voltage is applied to the thermoelectric cooling element 104, a temperature gradient can be established. In particular, thermoelectric cooling via the thermoelectric cooling element 104 can create a cooled face 514 proximate the microfluidic pathway 102 and a heated surface 516 proximate the heat sink 108. The fan 110 positioned proximate the heat sink 108 can facilitate establishing the temperature gradient. The sample 200 within the microfluidic pathway 102 can be in thermal communication with the cooled surface 514 of the thermoelectric cooling element 104, thereby causing the sample 200 to transition from the input temperature to the separation temperature, and the sample 200 to subsequently separate into the first phase 212 and the second phase 214.

Figure 6A:
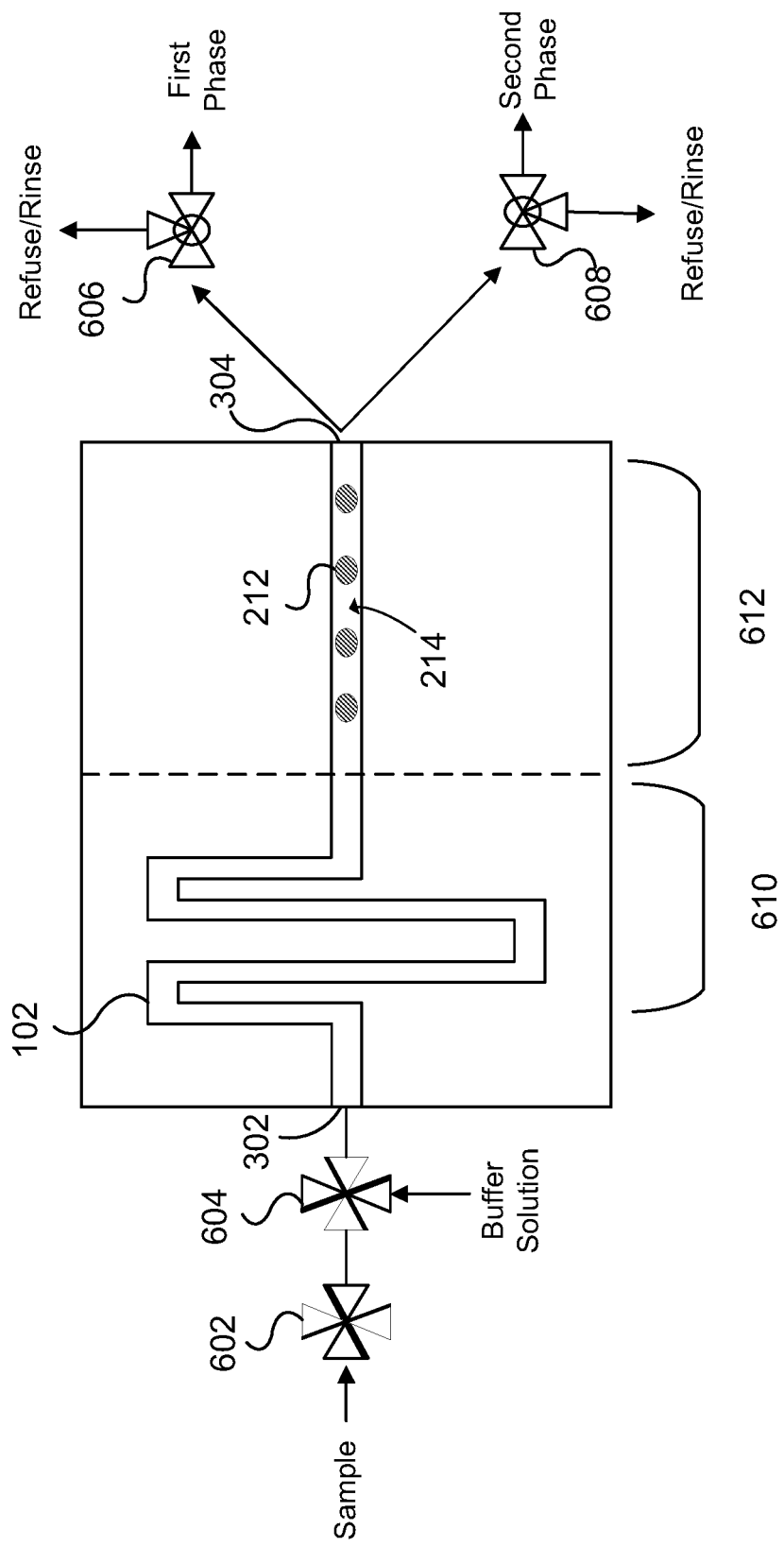
FIG. 6A is a schematic diagram of a microfluidic cooling device configured to operate in a continuous mode, according to some aspects of the present disclosure.

FIG. 6A illustrates a schematic diagram of the microfluidic cooling device 100 configured to operate in a continuous mode. The microfluidic pathway 102 can be prefilled with a buffer solution. The sample 200 can be continuously inserted into the microfluidic pathway 102 via a first valve 602 and a second valve 604 disposed upstream of the microfluidic pathway 102. The first valve 602 and the second valve 604 can be in electrical communication with the controller 402 such that a predetermined amount of the sample 200 at a predetermined flow rate can be inserted into the microfluidic pathway 102. In some embodiments, the first valve 602 and the second valve 604 can be configured to automatically insert the second liquid 204 upon the first liquid 202 being inserted into the microfluidic pathway 102. In some embodiments, the first valve 602 and the second valve 604 can be configured to automatically insert the first liquid 202 upon the second liquid 204 being inserted into the microfluidic pathway 102. Alternatively, in some embodiments, the first valve 602 and the second valve 604 can be configured to simultaneously insert the first liquid 202 and the second liquid 204. As the sample 200 flows through the microfluidic pathway 102, the initial volume of buffer solution can be displaced and can exit the microfluidic cooling device 100 via a third valve 606 and a fourth valve 608. The third valve 606 and the fourth valve 608 can be configured to direct the buffer solution to refuse lines.

In some embodiments, upon insertion into the microfluidic pathway 102, the sample 200 can flow through a mixing portion 610 of the microfluidic pathway 102. The mixing portion 610 can be a winding, twisting, and/or serpentine portion of the microfluidic pathway 102. The mixing portion 610 can ensure the plurality of analytes 210 is homogenously distributed throughout the sample 200. The mixing portion 610 can be disposed on or proximate an insulating base 620 such that the mixing portion 610 is not in thermal communication with the thermoelectric cooling element 104. This configuration can ensure that the sample 200 does not prematurely transition to the separation temperature, and thereby separate into the first phase 212 and the second phase 214. Upon flowing through the mixing portion 610, the sample 200 can flow through a separation portion 612 of the microfluidic pathway 102. The separation portion 612 can be in thermal communication with the thermoelectric cooling element 104 such that as the sample 200 flows through the separation portion 612, the temperature of the sample 200 can gradually decrease from the input temperature to the separation temperature. When the sample 200 is approximately the separation temperature, the sample 200 can separate into the first phase 212 and the second phase 214. As illustrated in FIG. 6A, in the continuous operation mode, upon separation, the first phase 212 and the second phase 214 can be alternating liquid slugs separated by a consistent length. Accordingly, the first phase 212 and the second phase 214 can continuously exit the microfluidic pathway 102 in an alternating pattern via the third valve 606 and the fourth valve 608, respectively. Once a predetermined volume of the sample 200 has been inserted into the microfluidic pathway 102 and subsequently separated and removed from the microfluidic pathway 102, thermoelectric cooling can be stopped and each valve can be rinsed with buffer solution. The buffer solution can be inserted into the microfluidic pathway 102 via the second valve 604. The third valve 606 and the fourth valve 608 can be configured to direct the buffer solution to refuse lines during rinsing.

Operating in continuous mode can provide various advantages, including the ability to provide inline introduction of the sample 200 and automated, precise flow control via the plurality of valves, enabling user free operation with maximum repeatability.

Figure 6B:
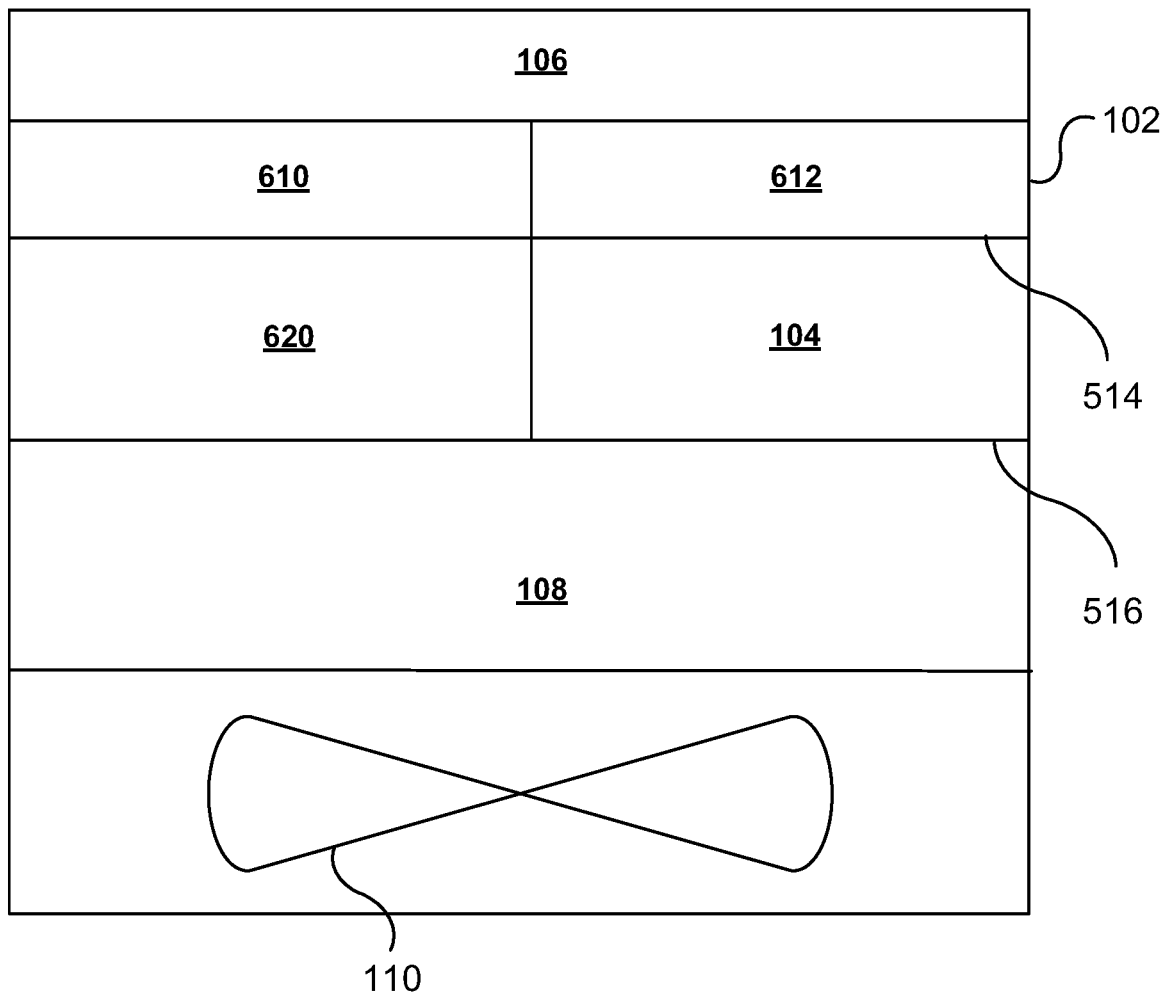
FIG. 6B is a cross-section view of the microfluidic cooling device of FIG. 6A, according to some aspects of the present disclosure.

FIG. 6B is a cross-section view of the microfluidic cooling device 100 of FIG. 6A. The microfluidic pathway 102 can be disposed proximate the thermoelectric cooling element 104 and an insulating base 620. The cover 106 can be positioned proximate the microfluidic pathway 102 to secure the microfluidic pathway 102 to the insulating base 620 and the thermoelectric cooling element 104. The mixing portion 610 of the microfluidic pathway 102 can be disposed proximate the insulating base 620, while the separation portion 612 of the microfluidic pathway 102 can be disposed proximate the thermoelectric cooling element 104. In this configuration, the sample 200 can ensure homogenous distribution of analytes 210 prior to thermoelectric cooling. As discussed herein, thermoelectric cooling via the thermoelectric cooling element 104 can create the cooled face 514 proximate the separation portion 610 and a heated surface 516 proximate the heat sink 108. The fan 110 positioned proximate the heat sink 108 can facilitate establishing the temperature gradient. The sample 200 within the separation portion 610 of the microfluidic pathway 102 can be in thermal communication with the cooled surface 514 of the thermoelectric cooling element 104, thereby causing the sample 200 to transition from the input temperature to the separation temperature, and the sample 200 to subsequently separate into the first phase 212 and the second phase 214.

Although FIGS. 6A and 6B illustrate one example configuration of a microfluidic cooling device 100 configured to operate in a continuous mode, it is contemplated that any configuration that provides for continuous flow of the sample 200 through the microfluidic pathway 102 and thus continuous output of the first phase 212 and the second phase 214 can be applied.

Figure 7:
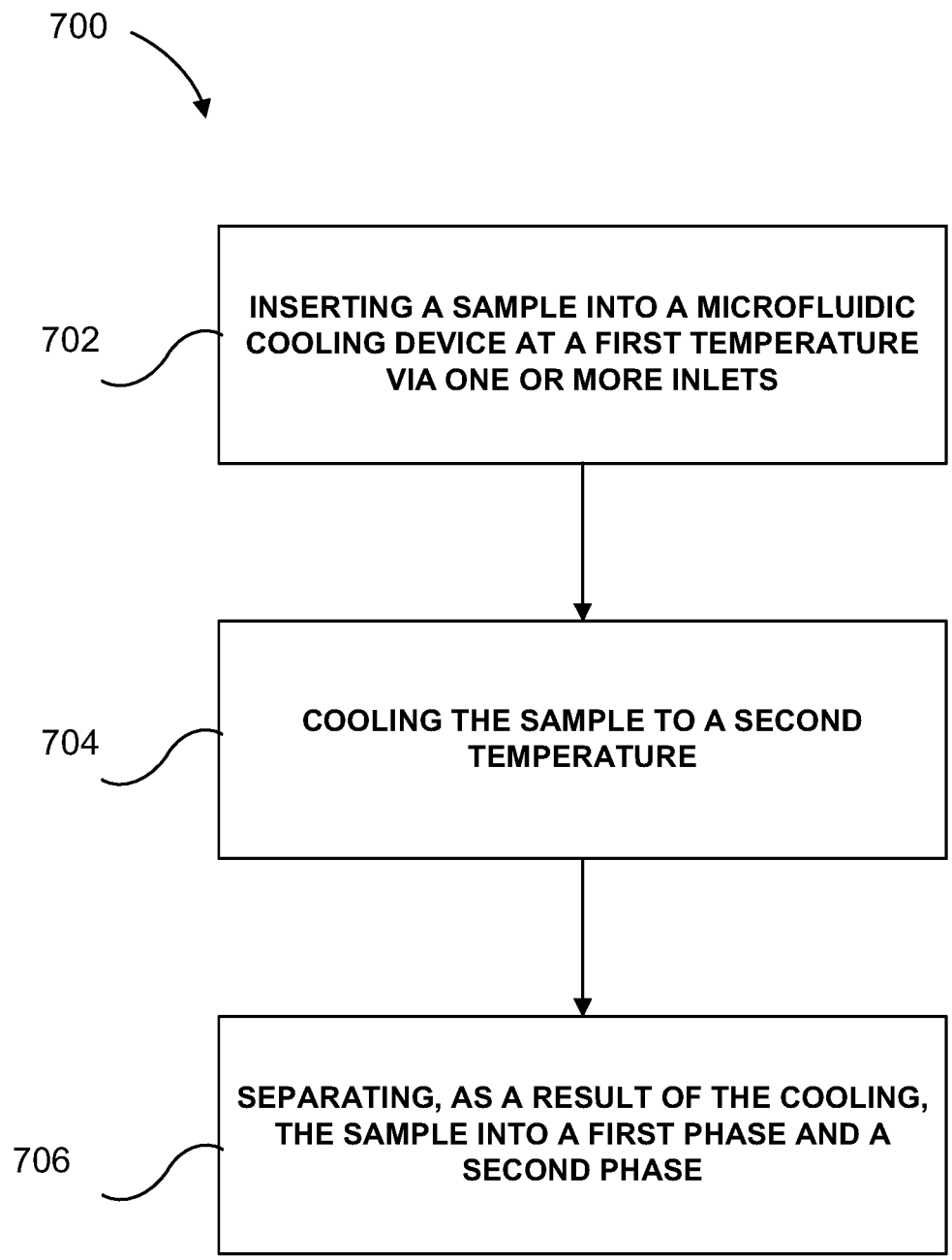
FIG. 7 is a flow diagram outlining a method of liquid-liquid phase separation, according to some aspects of the present disclosure.

FIG. 7 is a flow diagram outlining a method 700 of liquid-liquid phase separation via the microfluidic cooling device 100. The method can include inserting 702 a sample 200 into a microfluidic cooling device 100 at a first temperature (i.e., the input temperature) via one or more inlets 302. The sample can include the first liquid 202, the second liquid, and the plurality of soluble particles. The first liquid and the second liquid can be substantially miscible at the input temperature.

In some embodiments, the first liquid 202 can be inserted into the microfluidic cooling device 100 before inserting the second liquid 204. Alternatively, the second liquid 204 can be inserted into the microfluidic cooling device 100 before inserting the first liquid 202. In some embodiments, the first liquid 202 and the second liquid 204 can be inserted into the microfluidic cooling device simultaneously. In some embodiments, the first liquid 202 and the second liquid 204 are mixed prior to inserting, thus, the pre-mixed solution of the first liquid 202 and the second liquid 204 can then be inserted into the microfluidic cooling device 100.

The method 700 can further include cooling 704 the sample 200 to a second temperature (e.g., the separation temperature). The controller 402 can be in electrical communication with the one or more temperature sensors 406 in order to control the temperature of the thermoelectric cooling element 104 during thermoelectric cooling and provide precise and dynamic temperature regulation.

The method 700 can further include separating 706, as a result of the cooling, the sample 200 into a first phase 212 and a second phase 214. The first phase 212 can include a majority of the first liquid 202 and a portion of the soluble particles that are more soluble in the first liquid 202 than the second liquid 204. The second phase 214 can include a majority of the second liquid 204 and at a portion of the soluble particles that are more soluble in the second liquid 204. By way of example, the first phase 212 can include water as the first liquid 202 and the portion of the soluble particles that have a hydrophilic polarity, while the second phase 214 can include acetonitrile as the second liquid 204 and the portion of the soluble particles that have a hydrophobic polarity.

In some embodiments, the sample 200 can separate into the first phase 212 and the second phase 214 within approximately 5 seconds and approximately 60 seconds. In some embodiments, the sample 200 can separate into the first phase 212 and the second phase 214 within approximately 60 seconds an approximately 5 minutes. In some embodiments, the sample 200 can separate into the first phase 212 and the second phase 214 within between approximately 5 minutes and approximately 30 minutes.

The method 700 can further include analyzing the first phase 212. Alternatively or in addition to, the method 700 can further include analyzing the second phase 214. The first phase 212 and/or the second phase 214 can be analyzed by any known analysis technique, including but not limited to, mass spectrometry, chromatography, and the like.

The microfluidic cooling device 100 and the method 700 of liquid-liquid phase separation as discussed herein can be used in a variety of applications. By way of example, the microfluidic cooling device 100 can be used for desalination of aqueous samples for mass spectrometry analysis of hydrophobic and/or hydrophilic compounds. Additionally, the microfluidic cooling device 100 can be used for inline removal of acetonitrile as an intermediate step when performing high performance liquid chromatography and mass spectrometry for protein analysis. In this application, the first phase (e.g., the aqueous phase including proteins) 212 can be further analyzed, while the second phase (e.g. acetonitrile rich phase) 214 can be discarded. The microfluidic cooling device 100 can also be used for sample preparation with integrated cell lysis for intracellular metabolomics. In this application, a cell laden sample can be inserted into the microfluidic pathway 102. The microfluidic cooling device 100 can be configured to operate in the batch mode. After rinsing the sample with aqueous buffer, the cells can be lysed. Acetonitrile can be inserted into the microfluidic pathway 102 until the desired final compositions of the first phase 212 and second phase 214 have been achieved. Thermoelectric cooling can be initiated, and the sample can separate into a first phase 212 and the second phase 214. The second phase 214, including a majority of the acetonitrile and hydrophobic compounds can be further analyzed.

Additionally, the microfluidic cooling device 100 can be used to facilitate control of chemical reactions. By way of example, the sample 200 can include one or more reactive species. The reactive species can react within the sample 200 for a predetermined time such that the reactive species reacts to a predetermined degree. Upon the reactive species reacting to the predetermined degree, thermoelectric cooling via the microfluidic cooling device 100 can be initiated, thereby separating the initial reactive agents and/or intermediate reactive products based on solubility. The thermoelectric cooling and subsequently separation can prevent further reaction of the reactive species. This application can be particularly advantageous as it can provide an initially high mass transfer because the sample 200 can be a single homogenous phase, and subsequently significantly reduce mass transfer through thermoelectric cooling and phase separation.

In another application, the microfluidic cooling device 100 can be used for preparation of the sample 200 for Nuclear Magnetic Resonance (NMR) and Raman spectroscopy. Lipids can disrupt identification of the plurality of analytes 210, including metabolites and proteins, within the sample 200 during NMR spectroscopy. Accordingly, thermoelectric cooling via the microfluidic cooling device 100 can be used to isolate lipids within the second phase 214 (e.g., the acetonitrile rich phase) while a majority of the plurality of analytes 210 can remain in the first phase 212 (e.g., aqueous rich phase). The first phase 212 and the second phase 214 can subsequently be analyzed by NMR spectroscopy. Moreover, the presence of water can produce background fluorescence, thereby reducing and/or hiding signals from analytes during Raman spectroscopy. Accordingly, the second phase 214 can be analyzed by Raman spectroscopy in order to obtain better identification of the analytes 210.

In an additional application, the portability of the microfluidic cooling device 100 can facilitate in situ preparation of the sample 200. Accordingly, the microfluidic cooling system 400 can provide a rapid method for collection of the sample 200, preparation of the sample 200 using thermoelectric cooling via the microfluidic cooling device 100, and analysis of the resulting phases 212, 214 at a single location. Similarly, in some embodiments, the sample 200 can be collected and prepared using the microfluidic cooling device 100 at a first location. The resulting phases 212, 214 can then be preserved by freezing and transporting to a second location (e.g., a lab) for further analysis.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

What is claimed is:

1. An inline microfluidic liquid-liquid phase separation system comprising:
    a device comprising:
        an inlet configured to receive a liquid sample at a first temperature, the liquid sample comprising a first liquid and a second liquid, the first liquid and the second liquid being miscible at the first temperature;
        an outlet;
        a microfluidic pathway extending from the inlet to the outlet; and
        a thermoelectric cooling element in thermal communication with at least a portion of the microfluidic pathway;
        wherein the microfluidic pathway is dimensionally configured such that upon cooling the liquid sample from the first temperature to a lower, second temperature prior to reaching the outlet, the liquid sample undergoes liquid-liquid phase separation to form a first phase of the liquid sample comprising a majority of the first liquid and a second phase of the liquid sample comprising a majority of the second liquid;
        wherein the thermoelectric cooling element is configured to transition the liquid sample from the first temperature to the second temperature; and
        wherein the device is configured such that the liquid sample, the first liquid, the second liquid, the first phase of the liquid sample and the second phase of the liquid sample remain in the liquid state throughout the device.

2. The system of claim 1 further comprising the liquid sample;
    wherein the first liquid is water; and
    wherein the second liquid is acetonitrile.

3. The system of claim 1 further comprising the liquid sample;
    wherein the first liquid and the second liquid are immiscible at the second temperature.

4. The system of claim 1 further comprising the liquid sample;
    wherein the liquid sample further comprises:
        soluble particles; and
        analytes;
    wherein the first phase of the liquid sample further comprises a first portion of the soluble particles, the first portion being more soluble within the first liquid than the second liquid;
    wherein the second phase of the liquid sample further comprises a second portion of the soluble particles, the second portion being more soluble within the second liquid than the first liquid; and
    wherein the analytes are homogenously distributed throughout the liquid sample at the first temperature.

5. The system of claim 1, wherein the first temperature is above a phase transition temperature of the liquid sample.

6. The system of claim 1, wherein the second temperature is below a phase transition temperature of the liquid sample.

7. The system of claim 1, wherein the microfluidic pathway is further dimensionally configured such that the thermoelectric cooling element transitions the liquid sample from the first temperature to the second temperature within 60 seconds.

8. The system of claim 1, wherein the microfluidic pathway has an inner diameter of between approximately 10 microns to approximately 250 microns.

9. The system of claim 8, wherein the microfluidic pathway comprises:
    a mixing portion configured to homogenously distribute the analytes within the liquid sample at the first temperature; and
    a separation portion in which the liquid sample undergoes the liquid-liquid phase separation into the first phase of the liquid sample and the second phase of the liquid sample at the second temperature.

10. The system of claim 1, wherein the microfluidic pathway is further configured to:
    continuously receive the liquid sample via the inlet; and
    continuously output the first phase of the liquid sample and the second phase of the liquid sample via the outlet.

11. A microfluidic cooling system for liquid-liquid phase separation comprising:
    a microfluidic cooling device comprising:
        a first microfluidic pathway comprising:
            one or more inlets configured to receive a sample at a first temperature, the sample comprising a first liquid, a second liquid, and a plurality of soluble particles, the first liquid and the second liquid being miscible at the first temperature; and
            one or more outlets configured to output a first phase of the sample and a second phase of the sample at a second temperature, the first phase comprising a majority of the first liquid and a first portion of the plurality of soluble particles, the first portion being more soluble within the first liquid than the second liquid, and the second phase comprising a majority of the second liquid and a second portion of the plurality of soluble particles, the second portion being more soluble within the second liquid than the first liquid;
        a thermoelectric cooling element in thermal communication with at least a portion of the microfluidic pathway and configured to transition the sample from the first temperature to the second temperature; and
        a controller in operative communication with the microfluidic cooling device and configured to cause the thermoelectric cooling element to transition the sample from the first temperature to the second temperature.

12. The microfluidic cooling system of claim 11, wherein the first liquid is water and the second liquid is acetonitrile.

13. The microfluidic cooling system of claim 12 further comprising a plurality of valves configured to insert a first predetermined amount of the first liquid and a second predetermined amount of the second liquid via the one or more inlets and output a first predetermined amount of the first phase and a second predetermined amount of the second phase.

14. The microfluidic cooling system of claim 13, wherein the plurality of valves is in electronic communication with the controller, the plurality of valves configured to automatically insert the second liquid into the microfluidic cooling device upon the first liquid being inserted into the microfluidic cooling device.

15. The microfluidic cooling system of claim 11, wherein the first liquid and the second liquid are immiscible at the second temperature.

16. The microfluidic cooling system of claim 11, wherein the sample further comprises a plurality of analytes, the plurality of analytes being homogenously distributed throughout the sample at the first temperature.

17. The microfluidic cooling system of claim 16, wherein the plurality of analytes is more soluble in the first liquid than the second liquid.

18. The microfluidic cooling system of claim 17, wherein the first phase comprises the plurality of analytes.

19. The microfluidic cooling system of claim 16, wherein the plurality of analytes is more soluble in the second liquid than the first liquid.

20. The microfluidic cooling system of claim 19, wherein the second phase comprises the plurality of analytes.

21. The microfluidic cooling system of claim 11, wherein the controller comprises a graphical user interface configured to receive user inputs for a plurality of operative parameters.

22. The microfluidic cooling system of claim 11 further comprising a plurality of sensors configured to measure a temperature of the thermoelectric cooling element.

23. The microfluidic cooling system of claim 11 further comprising a power supply in operative communication with the thermoelectric cooling element.

24. The microfluidic cooling system of claim 11, wherein the controller is further configured to regulate a temperature of the thermoelectric cooling element.

25. The microfluidic cooling system of claim 24, wherein the temperature of the thermoelectric cooling element is regulated based at least in part on phase equilibrium data of the sample.

26. A method of liquid-liquid phase separation comprising:
   providing a sample into a microfluidic pathway, the sample comprising a first liquid, a second liquid, and a plurality of soluble particles, the first liquid and the second liquid being miscible at a first temperature;
   cooling the sample as it flows through at least a portion of the microfluidic pathway from the first temperature to a second temperature; and
   separating a first phase of the sample from a second phase of the sample downstream of the microfluidic pathway, the first phase comprising a majority of the first liquid and a first portion of the plurality of soluble particles, the first portion being more soluble in the first liquid than the second liquid, and the second phase comprising a majority of the second liquid and a second portion of the plurality of soluble particles, the second portion being more soluble in the second liquid than the first liquid;
   wherein during the providing, cooling, and separating, the sample, the first liquid, the second liquid, the first phase of the sample and the second phase of the sample remain in the liquid state.

27. The method of claim 26, wherein the first liquid is water and the second liquid is acetonitrile.

28. The method of claim 26, wherein the sample further comprises a plurality of analytes homogenously distributed throughout the sample at the first temperature.

29. The method of claim 26, wherein providing the sample into the microfluidic pathway comprises providing the first liquid before providing the second liquid.

30. The method of claim 26, wherein providing the sample into the microfluidic pathway comprises providing the first liquid and the second liquid simultaneously.

31. The method of claim 26, wherein the second temperature is below a phase transition temperature of the sample.

32. The method of claim 26, wherein the cooling and separating occurs within 60 seconds.

33. The method of claim 26, wherein providing the sample comprises continuously providing the sample into the microfluidic pathway.

* * * * *